(12) United States Patent
Lei et al.

(10) Patent No.: US 11,617,805 B2
(45) Date of Patent: Apr. 4, 2023

(54) LIGHT AND DISINFECTION SYSTEM WITH COINCIDENT ILLUMINATION RANGE

(71) Applicant: Consumer Lighting (U.S.), LLC, Norwalk, CT (US)

(72) Inventors: Ming Lei, Shanghai (CN); Huisheng Zhou, Shanghai (CN)

(73) Assignee: SAVANT TECHNOLOGIES LLC, Norwalk, CT (US)

( * ) Notice: Subject to any disclaimer, the term of this patent is extended or adjusted under 35 U.S.C. 154(b) by 2 days.

(21) Appl. No.: 16/667,891

(22) Filed: Oct. 29, 2019

(65) Prior Publication Data

US 2020/0188542 A1 Jun. 18, 2020

(30) Foreign Application Priority Data

Oct. 29, 2018 (CN) .......................... 201811269817.3

(51) Int. Cl.
*A61L 2/10* (2006.01)
*A61L 2/08* (2006.01)
*A61L 2/24* (2006.01)

(52) U.S. Cl.
CPC ...... *A61L 2/08* (2013.01); *A61L 2/10* (2013.01); *A61L 2/24* (2013.01); *A61L 2202/11* (2013.01); *A61L 2202/14* (2013.01)

(58) Field of Classification Search
CPC .......... A61L 2/08; A61L 2/24; A61L 2202/14; A61L 2202/11; A61L 2/10; F21V 14/02; F21V 23/0464; F21V 23/0471; F21V 3/00; F21V 33/00; F21V 23/003; F21V 23/04; F21S 4/28; F21S 8/00; F21Y 2103/10; F21Y 2115/10
See application file for complete search history.

(56) References Cited

U.S. PATENT DOCUMENTS

| | | | |
|---|---|---|---|
| 7,612,492 B2 * | 11/2009 | Lestician | A61L 2/10 422/186 |
| 8,097,861 B2 * | 1/2012 | Leben | B66B 11/024 250/365 |
| 9,513,113 B2 | 12/2016 | Yang | |
| 10,792,381 B2 * | 10/2020 | Poulsen | A61L 2/10 |
| 10,960,091 B2 * | 3/2021 | Dijkstra | H05B 47/125 |

(Continued)

FOREIGN PATENT DOCUMENTS

| CN | 102878459 A | 1/2013 |
|---|---|---|
| CN | 104919272 A | 9/2015 |

(Continued)

OTHER PUBLICATIONS

Office Action for Canadian Patent Appl. No. 3,060,616, dated Mar. 17, 2021, 5 pages.

(Continued)

*Primary Examiner* — Wyatt A Stoffa
(74) *Attorney, Agent, or Firm* — Wood IP LLC

(57) ABSTRACT

The present disclosure relates to a light and disinfection system, comprising: a lighting system which includes an illumination source and a diffusion hood suitable for the illumination source; a disinfection system which includes a disinfection light source and a cover adapted to transmit the disinfection light source, wherein the diffusion hood and the cover are respectively used for the illumination source and the disinfection light source.

18 Claims, 3 Drawing Sheets

(56) References Cited

U.S. PATENT DOCUMENTS

| | | | | |
|---|---|---|---|---|
| 2004/0084630 | A1* | 5/2004 | Waluszko | A61L 2/10 250/455.11 |
| 2007/0053188 | A1* | 3/2007 | New | B60Q 3/43 362/276 |
| 2009/0129974 | A1* | 5/2009 | McEllen | A61L 9/205 422/108 |
| 2010/0187443 | A1* | 7/2010 | Leben | A61L 2/10 250/492.1 |
| 2011/0181200 | A1* | 7/2011 | Luk | H05B 45/20 315/294 |
| 2013/0062534 | A1 | 3/2013 | Cole | |
| 2013/0234041 | A1* | 9/2013 | Deal | G01J 1/429 250/455.11 |
| 2013/0235573 | A1* | 9/2013 | Ricci | F21V 9/06 362/235 |
| 2014/0183377 | A1* | 7/2014 | Bettles | A61L 2/10 250/455.11 |
| 2014/0271348 | A1* | 9/2014 | Deal | A61L 2/28 250/492.1 |
| 2015/0062893 | A1* | 3/2015 | Lynn | F21V 7/00 362/231 |
| 2015/0090903 | A1* | 4/2015 | Cole | A61L 2/10 250/492.1 |
| 2015/0359915 | A1* | 12/2015 | Farren | H01J 37/244 250/492.1 |
| 2016/0121007 | A1* | 5/2016 | Dayton | A61L 2/10 250/492.1 |
| 2016/0296650 | A1* | 10/2016 | Liao | A61L 2/10 |
| 2017/0049915 | A1* | 2/2017 | Brais | H05B 47/115 |
| 2017/0100495 | A1* | 4/2017 | Shur | A61L 2/10 |
| 2017/0340760 | A1* | 11/2017 | Starkweather | A61L 2/24 |
| 2017/0368215 | A1* | 12/2017 | Shatalov | H04N 5/332 |
| 2018/0021465 | A1* | 1/2018 | Dobrinsky | E03D 9/08 4/233 |
| 2018/0193499 | A1* | 7/2018 | Lu | A61L 2/10 |
| 2019/0060495 | A1* | 2/2019 | Gil | A61L 2/10 |
| 2019/0070324 | A1* | 3/2019 | Hardin | A61L 2/24 |
| 2019/0142981 | A1* | 5/2019 | Kim | G01B 11/02 250/455.11 |
| 2019/0201570 | A1* | 7/2019 | Dobrinsky | G01N 21/94 |
| 2019/0298869 | A1* | 10/2019 | Poulsen | F21S 8/063 |
| 2020/0102695 | A1* | 4/2020 | Khizar | A61L 2/10 |

FOREIGN PATENT DOCUMENTS

| | | |
|---|---|---|
| CN | 106195674 A | 12/2016 |
| KR | 20060110025 A | 10/2006 |
| KR | 10-20160148140 A | 12/2016 |

OTHER PUBLICATIONS

Office Action for Chinese Patent Appl. No. 201811269817.3, dated May 17, 2021, 13 pages.

\* cited by examiner

LIGHT AND DISINFECTION SYSTEM WITH COINCIDENT ILLUMINATION RANGE

FIELD

The present disclosure generally relates to a system for disinfection and sterilization using light, more specifically to a system with functions of both lighting and disinfection or sterilization.

BACKGROUND

It is found that ultraviolet, violet or blue light may have a function of disinfection and sterilization, such as inactivation of pathogen on an object surface, in the air or water. The pathogen refers to any microscopic organism that can cause disease or infection in human body, including bacteria, viruses, spores and fungi. Inactivation includes killing the pathogen, making it unable to reproduce, or making it unable to infect human. The ultraviolet (UV) refers to light having a wavelength in a range of 100 nm to 400 nm; four sub-ranges of the UV range comprises a vacuum UV ranging from 100 nm to 200 nm; a UVC ranging from 200 nm to 280 nm; a UVB ranging from 280 nm to 315 nm; and a UVA ranging from 315 nm to 400 nm. The wavelength of the violet light is about 400 nm to about 450 nm; the wavelength of the blue light is about 450 nm to about 490 nm.

However, exposure to the light of UV wavelength may be harmful to human. Therefore, a UV sterilization system can only be used safely in places where personnel are absent or cannot access. An inactivation rate at which the violet, blue or visible light with longer wavelength inactivates the most common pathogen is lower than that of the UV range by three to five magnitudes. Therefore, disinfection using visible light requires sufficient luminous flux density, which needs to consume more electric energy. Moreover, if the violet or blue light is used for disinfection, luminous flux of violet light within a space the human body occupies would be very large, which will cause eye fatigue, headache, nausea, dizziness or discomfort to human.

SUMMARY

In one embodiment, the present application discloses a lighting disinfection system comprising a lighting system which includes an illumination source and a diffusion hood suitable for the illumination source; a disinfection system which includes a disinfection light source and a cover adapted to transmit the disinfection light source, wherein the diffusion hood and the cover are respectively used for the illumination source and the disinfection light source.

BRIEF DESCRIPTION OF THE DRAWINGS

These and other features, aspects and advantages of the present invention can be understood better in light of the following detailed description with reference to the accompanying drawings, in which similar reference signs represent similar components in the whole drawings, in which.

DETAILED DESCRIPTION

In order to help the person skilled in the art to exactly understand the subject matters claimed by the present invention, detailed description for embodiments of the present invention will be given with reference to the accompanying drawings in the following. In the following detailed description for those embodiments, some known functions or structures will not be described in details by the Description, to avoid disclosure of the present invention to be affected by unnecessary details.

Unless defined otherwise, the technical or scientific terms used in the Claims and the Description should have meanings as commonly understood by one of ordinary skilled in the art to which the present disclosure belongs. The terms "first", "second" and the like in the Description and the Claims do not mean any sequential order, quantity or importance, but are only used for distinguishing different components. The terms "a", "an" and the like do not denote a limitation of quantity, but denote the existence of at least one. Unless pointed out otherwise, terms such as "front", "rear", "lower" and/or "upper" and the like are used only for convenient explanation, rather than limiting to one position or one space orientation. "Or" and the like mean inclusive, and refer to one or all of the illustrated terms. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, but may comprise electric connection or coupling, no matter directly or indirectly.

Figure 1:
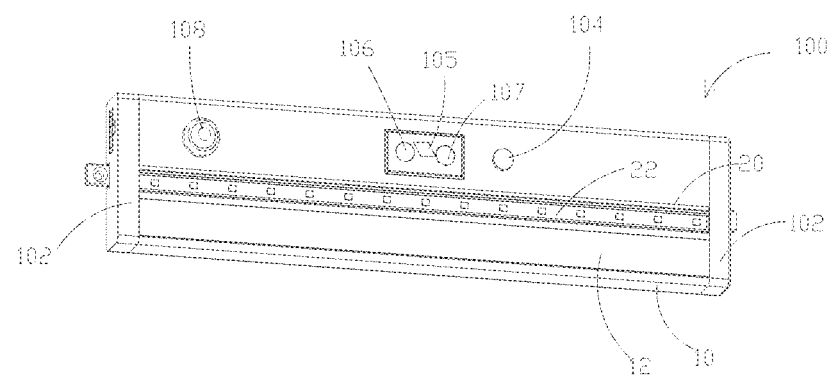
FIG. 1 is an external view of a lighting disinfection system according to one embodiment of the present invention.
Figure 2:
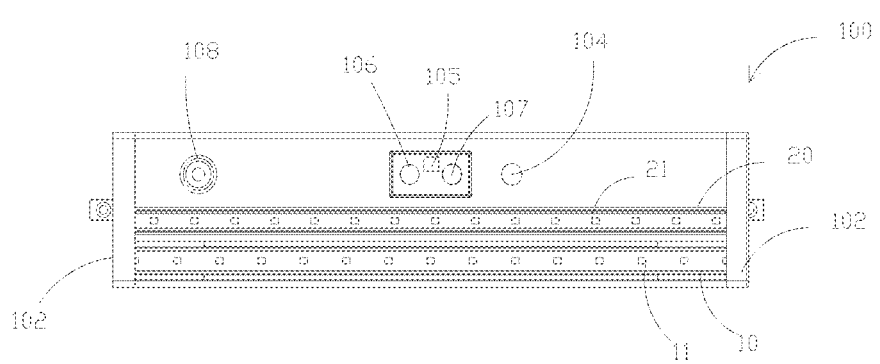
FIG. 2 is a front view of a lighting disinfection system according to one embodiment of the present invention, with the diffusion hood removed.
Figure 3:
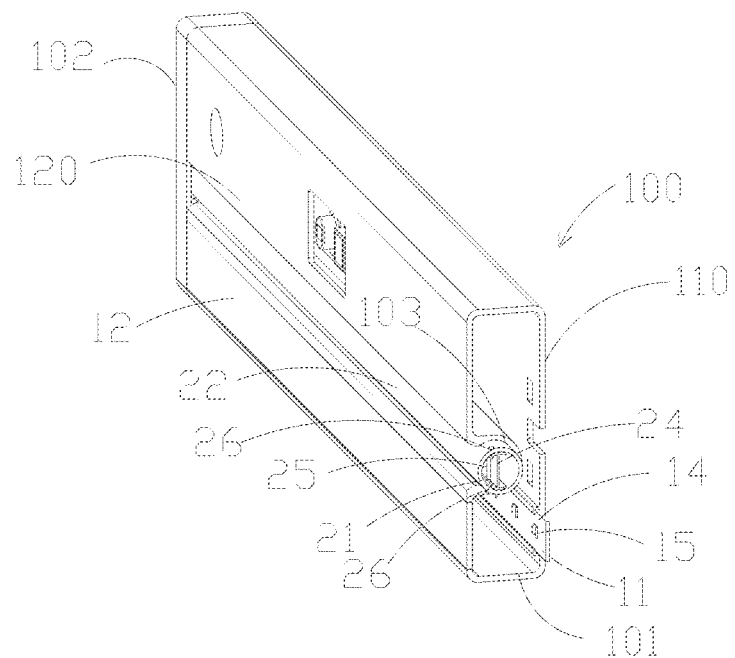
FIG. 3 is an internal schematic diagram of a lighting disinfection system according to one embodiment of the present invention, with one end removed.
Figure 4:
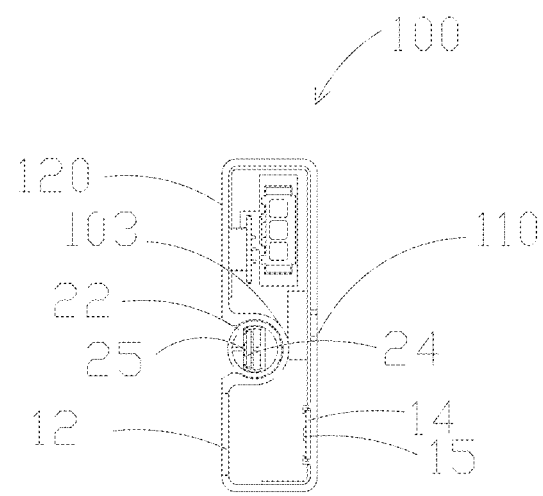
FIG. 4 is a side cross-sectional view according to one embodiment of the present invention, with the illumination source and the disinfection light source having the same illumination direction.

As shown in FIG. 1 and FIG. 2, the present application discloses a lighting disinfection system 100, comprising a lighting system 10 that includes an illumination source 11 and a diffusion hood 12 suitable for the illumination source; a disinfection system 20 that includes a disinfection light source 21 and a cover 22 adapted to transmit the disinfection light source, wherein the diffusion hood 12 and the cover 22 are respectively used for the illumination source 11 and the disinfection light source 21.

In one embodiment, the illumination source 11 comprises a white light source, e.g., white LED. In one embodiment, the disinfection light source 21 comprises a UV light source, including vacuum UV, UVC, UVB, UVA and the like, preferably a light source having a wavelength ranging from 280 nm to 380 nm, or visible light source such as violet and blue light. Since the diffusion hood for the illumination source, e.g., Polycarbonate (PC), PMMA, PBT and the like all have a lower light transmittance of UV light source, if only the diffusion hood for the illumination source is used as both the diffusion hood for the illumination source and the UV light source, the transmittance of the UV light source will become low, and the UV light source will cause yellow light effect of the diffusion hood for the illumination source. If a diffusion hood suitable for both the illumination source and the UV light source is selected, a higher cost will be caused. Moreover, the light emitted from the UV light source is not visible, its cover does not need to be a diffusion hood for the illumination source with a very high diffusion, but may use material with a transmittance of UV light being 80% or more as the cover. For example, quartz glass and similar material may be used as the cover of the UV light source in the specific embodiments of the present application. The usage of quartz glass as the cover of the UV light source may achieve a transmittance of 97%, which is higher than the transmittance of violet light source, i.e., 73%-78% that can be achieved by sharing the same white light diffusion hood by a UV light source and a white light source. In one embodiment, PC, PMMA, PBT and the similar material serve as the diffusion hood of the white light LED source in one specific embodiment of the present application. Therefore, in the embodiments of the present application, the lighting system and the disinfection system use their own diffusion hood and cover respectively, which may allow the illumination source and the disinfection light source to achieve their own best effects at low cost.

The lighting disinfection system 100 of the present application may be used to be mounted at a bottom of a kitchen cabinet, above a countertop, for lighting the countertop of the kitchen and performing disinfection and sterilization thereon. The lighting disinfection system 100 is preferably disposed within a distance of 0.5 m-2 m above the countertop. If it is disposed at a distance of 0.5 m, the radiation power of the disinfection system is preferably 3-10 W/m$^2$. The lighting disinfection system of the present application can also be used in a bathroom, home table, office space, laundry room, wardrobe, office dining room and any other places that need disinfection, sterilization and lighting. The lighting disinfection system 100 may perform the function of lighting when needing lighting, and perform the function of disinfection and sterilization when people leave so as to provide a clean and hygienic place.

As shown in FIGS. 1-5, in one embodiment of the present application, the lighting disinfection system 100 comprises a housing 101 for accommodating the lighting system 10 and the disinfection system 20. In a specific embodiment, the housing 101 comprises a bottom part 110, a front part 120 and two ends 102 in a longitudinal direction, forming an internal space, wherein the lighting system 10 and the disinfection system 20 extend between the two ends 102 respectively, and are mounted within the internal space in parallel.

In one embodiment, the illumination source 11 comprises a metal core printed circuit board (MCPCB) 14 mounted inside the housing and an illumination source chip 15 mounted on the MCPCB, and the diffusion hood 12 is mounted on an opening in front of the corresponding illumination source chip 15 of the front part 120 of the housing 101. The illumination source chip 15 may be one or more, and in case of more than one, the illumination source chips are provided on a long-striped MCPCB 14 in intervals.

In one embodiment, the front part 120 of the housing 101 forms an inward depression near the diffusion hood 12, creating a slot 103 between the two ends 102. The disinfection light source 21 comprises a MCPCB 24 having a UV-protective solder mask mounted inside the slot 103, at the bottom part of the disinfection housing, and a disinfection light source chip 25 (e.g., UV light source chip) mounted on the MCPCB 24 having a UV-protective solder mask. In one embodiment, the cover 22 is mounted on the slot 103, for covering the slot 103. In another embodiment, the cross section of the slot 103 is arc-shaped, and the cover 22 is a hollow cylinder disposed rotatably and horizontally within the slot 103. The MCPCB 24 and the disinfection light source chip 25 of the disinfection light source 21 are placed within the hollow cylinder of the cover 22. The UV light source chips may be one or more, and in case of more than one, the UV light source chips are provided on a long-striped MCPCB 24 having a UV-protective solder mask in intervals.

Figure 5:
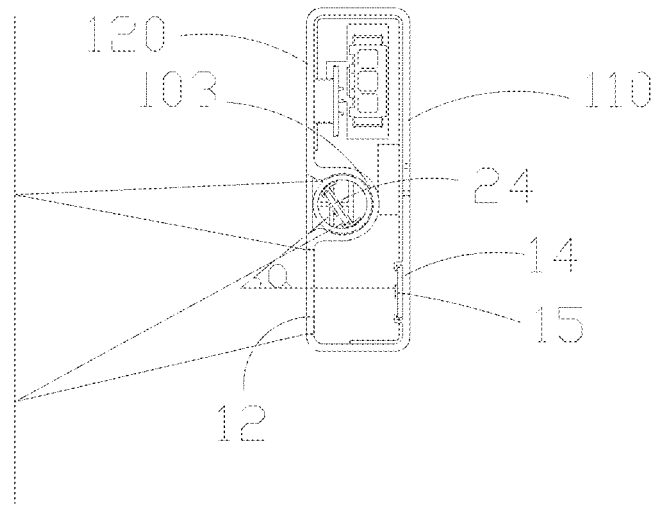
FIG. 5 is a side cross-sectional view according to one embodiment of the present invention, with an angle formed between the illumination directions of the illumination source and the disinfection light source.

As shown in FIG. 5, there is an angle 'a' formed between the disinfection light source 21 and the illumination source 11, such that the disinfection light source 21 of the disinfection system 20 and the illumination source 11 of the lighting system 10 that are mounted adjacently have a substantially coincident illumination range on an illumination face. In one embodiment, an illumination area of the disinfection light source 21 is adjusted by rotating the cover 22 to drive the disinfection light source chip 25 to rotate for an angle.

Figure 6:
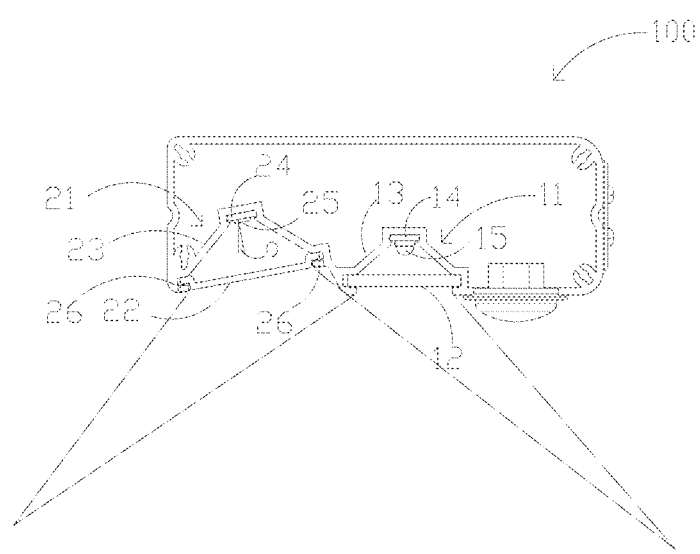
FIG. 6 is a horizontal cross-sectional view according to another embodiment of the present invention.

As shown in FIG. 6, in another embodiment, the illumination source 11 comprises a first housing 13, an MCPCB 14 mounted at the bottom part of the lighting housing, and an illumination source chip 15 mounted on the MCPCB. The first housing 13 extends at the bottom part from two sides of the MCPCB 14 obliquely upward, forming an enlarged opening on which the diffusion hood 12 is mounted. The illumination source chip 15 may be one or more as shown in FIG. 2, and in case of more than one, the illumination source chips are provided on the MCPCB 14 in intervals.

The disinfection light source 21 comprises a second housing 23, an MCPCB 24 having a UV-protective solder mask mounted at the bottom part of the disinfection housing, and a disinfection light source chip 25 mounted on the MCPCB 24 having a UV-protective solder mask, e.g., UV light source chip. The second housing 23 extends at the bottom part from two sides of the MCPCB 24 having a UV-protective solder mask obliquely upward, forming an enlarged opening on which the cover 22 is mounted. The UV light source chips may be one or more as shown in FIG. 2, and in case of more than one, the UV light source chips are provided on an MCPCB 24 having a UV-protective solder mask in intervals.

There is an angle 'a' formed between the disinfection light source 21 and the illumination source 11, such that the disinfection light source 21 of the disinfection system 20 and the illumination source 11 of the lighting system 10 that are mounted adjacently have a substantially coincident illumination range on an illumination face. In one embodiment, an illumination area of the disinfection light source 21 is adjusted by rotating the second housing 23 to drive the disinfection light source chip 25 to rotate for an angle.

As shown in FIG. 5, when the disinfection light source 21 comprises a UV light source, since the UV light source is invisible, it is quite difficult to know which areas can actually be illuminated by the UV light source. In one embodiment of the present application, the disinfection system 20 comprises at least one laser emitter 26 mounted at an edge of the cover 22, near the disinfection chip 24. The at least one laser emitter 26 is used to emit laser to mark a disinfection range that the UV light source can illuminate on the illumination face. There may be a pair of laser emitters, mounted at edges of the cover 22 corresponding to the two sides of the disinfection chip 24 respectively, which may be mounted at an edge of inner side or an edge of outer side of the cover 22. When the disinfection area needs to be adjusted, the laser emitter 26 positioned at an edge of the cover 22 of the disinfection light source is turned on to emit laser beams. The disinfection area can be determined according to an emission area marked by the laser beams. As the cover 22 in a shape of hollow cylinder is rotated, the laser emitter 26 moves as well, and at this time the laser marked area will also change accordingly. When the disinfection area marked by the laser is adjusted to a desired position, the laser emitter 26 is turned off. In FIG. 6, the laser emitters 26 are mounted on two sides in the front of the cover.

The UV light source can be turned on or turned off by a motion sensor 104. In one example, if waving a hand or some other article(s) in any direction within 3 seconds to pass through the motion sensor 104, the UV light source can be turned on or turned off. The lighting disinfection system 20 of the present application further comprises a built-in timer 105. The timing starts after the UV light source is turned on, and the UV light source will automatically be turned off after the timing reaches a preset time, so as to ensure that the disinfection effect reaches an expected level.

In order to ensure that the user would not be irradiated by the UV light, in one embodiment, the lighting disinfection system 100 of the present application further comprises a detecting sensor 106 mounted on the lighting disinfection system, such as infrared sensor, ultrasound sensor, microwave sensor and the like, for detecting whether anybody is nearby when the UV light source is turned on. If it is detected that someone is nearby, the UV light source will temporarily be turned off; until it is detected that the person is no longer in the detected region of the sensor, the UV light source will be turned on again. The detecting sensors 106 are mounted on the two ends 102 of the housing 101 respectively, so as to ensure that the coverage of the detecting sensors can detect activities of people around.

In one embodiment, the lighting disinfection system of the present application further comprises a photosensitive sensor 107 mounted on the lighting disinfection system. When the UV light source is turned on at night, if the photosensitive sensor detects light that exceeds a preset threshold, it indicates that someone conducts activities with light on, then the UV light source will temporarily be turned off; until the photosensitive sensor detects light that does not exceed the preset threshold, then the UV light source will be turned on again.

For the timer 105 of the lighting disinfection system of the present application, timing will stop when the UV light source is turned off temporarily, and timing will resume when the UV light source is turned on again, so as to ensure that a total time of illumination of the UV light source reaches a predetermined value, thus achieving the best effect of disinfection and sterilization.

In FIGS. 1-2, the lighting disinfection system of the present application further comprises an indicator 108, e.g., an indicator light, for indicating the working status of the disinfection system. For example, when the disinfection system is working, the indicator light is on; when the disinfection system is turned off, the indicator light is off; and when the disinfection system is turned off temporarily, the indicator light is flickering.

The motion sensor 104, timer 105, detecting sensor 106, photosensitive sensor 107 and indicator 108 in the present application can all be mounted at different positions, instead of the positions defined in the figures. For example, they can also be mounted on the two ends 102 of the housing 101.

Although the present invention has been set forth in details in combination with specific embodiments, the person skilled in the art shall be understood that many modifications and variations may be made to the present invention. Therefore, it should be recognized that the intention of the claims is to cover all these modifications and variations within the real concept and range of the present invention.

What is claimed is:

1. A lighting disinfection system, comprising:
   a system housing comprising two cavities or depressions on a front part of the system house, each cavities or depressions forming one of a light system housing and a disinfection system housing;
   a lighting system comprising an illumination source placed inside the light system housing, and a diffusion hood covering the illumination source;
   a disinfection system comprising a disinfection light source placed inside the disinfection system housing and a cover covering the disinfection light source, wherein the cover is capable of transmitting 80% or more disinfection light generated by the disinfection light source,
   wherein the cover of the disinfection light source and the diffusion hood of the illumination source are both situated by the front part of the system housing to allow a illumination light and a disinfection light to irradiate from the front part of the system housing,
   wherein an orientation of the disinfection light source is adjustable relative to an orientation of the illumination source and an illumination area of the disinfection light source is adjusted by rotating the disinfection light source,
   wherein the system housing comprises a bottom part, the front part and two ends in a longitudinal direction of the bottom part and the front part, connecting the bottom part and front part, forming an internal space, wherein the two cavities or depressions on the front part of the system housing extend between the two ends in the longitudinal direction of the internal space, forming the light system housing and the disinfection system housing to house the lighting system and the disinfection system between the two ends in the longitudinal direction of the internal space respectively,
   wherein the front part of the system housing forms an inward depression near the lighting system, creating a slot between the two ends to form the disinfection system housing,
   wherein the disinfection light source comprises a disinfection light source chip that is mounted inside the disinfection system housing, and
   wherein the cover comprises a hollow cylinder rotatably disposed within the slot, and an illumination area of the disinfection light source is adjusted by rotating the cover to drive the disinfection light source chip to rotate for an angle.

2. The system according to claim 1, wherein the disinfection light source of the disinfection system and the illumination source of the lighting system that are mounted adjacently and there is an angle formed between the disinfection light source and the illumination source such that the disinfection light source of the disinfection system and the illumination source of the lighting system have a coincident illumination range on an irradiated object.

3. The system according to claim 1, wherein the illumination source comprises an illumination source chip mounted within the light system housing, and the diffusion hood is mounted on an opening of the light system housing in front of the corresponding illumination source chip in the front part of the system housing.

4. The system according to claim 1, wherein the disinfection system comprises at least one laser emitter mounted at an edge of the cover, the at least one laser emitter being used for emitting laser to mark a disinfection range that the disinfection light source can illuminate on an illumination face.

5. The system according to claim 1, further comprising a detecting sensor or photosensitive sensor mounted on the lighting disinfection system, wherein the disinfection light source will be turned off when the detecting sensor detects that someone is nearby or the photosensitive sensor detects light that exceeds a preset threshold.

6. The system according to claim 1, further comprising a timer, which stops timing when the disinfection light source is turned off temporarily and resumes timing when the disinfection light source is turned on again, so as to ensure that a total time of illumination of the disinfection light source reaches a predetermined value.

7. The system according to claim 1, wherein the disinfection light source is a UV light.

8. A lighting disinfection system, comprising:
a system housing comprising two cavities or depressions on a front part of the system house, each cavities or depressions forming one of a light system housing and a disinfection system housing;
a lighting system having an illumination source placed inside the light system housing, and a diffusion hood covering the illumination source;
a disinfection system having a disinfection light source placed inside the disinfection system housing and a cover covering the disinfection light source, wherein the cover is capable of transmitting 80% or more disinfection light generated by the disinfection light source;
wherein the cover of the disinfection light source and the diffusion hood of the illumination source are both situated by the front part of the system housing to allow a illumination light and a disinfection light to irradiate from the front part of the system housing,
wherein orientation of at least one of the illumination source or disinfection light source is adjustable to have a coincident illumination range on an irradiated object, and
wherein the system housing comprises a bottom part, the front part and two ends in a longitudinal direction of the bottom part and the front part, connecting the bottom part and front part, forming an internal space, wherein the two cavities or depressions on the front part of the system housing extend between the two ends in the longitudinal direction of the internal space, forming the light system housing and the disinfection system housing to house the lighting system and the disinfection system between the two ends in the longitudinal direction of the internal space respectively,
wherein the front part of the system housing forms an inward depression near the lighting system, creating a slot between the two ends to form the disinfection system housing,
wherein the disinfection light source comprises a disinfection light source chip that is mounted inside the disinfection system housing, and
wherein the cover comprises a hollow cylinder rotatably disposed within the slot, and an illumination area of the disinfection light source is adjusted by rotating the cover to drive the disinfection light source chip to rotate for an angle.

9. The lighting disinfection system according to claim 8, wherein the disinfection system comprises at least one laser emitter mounted at an edge of the cover, the at least one laser emitter being used for emitting laser to mark a disinfection range that the disinfection light source can illuminate on an illumination face.

10. The lighting disinfection system according to claim 8, further comprising a detecting sensor or photosensitive sensor mounted on the lighting disinfection system, wherein the disinfection light source will be turned off when the detecting sensor detects that someone is nearby or the photosensitive sensor detects light that exceeds a preset threshold.

11. The lighting disinfection system according to claim 8, further comprising a timer, which stops timing when the disinfection light source is turned off temporarily and resumes timing when the disinfection light source is turned on again, so as to ensure that a total time of illumination of the disinfection light source reaches a predetermined value.

12. The lighting disinfection system according to claim 8, wherein the disinfection light source and the illumination source are mounted adjacently.

13. The lighting disinfection system according to claim 12, wherein there is an angle formed between the disinfection light source and the illumination source such that the disinfection light source of the disinfection system and the illumination source of the lighting system have a coincident illumination range on an irradiated object.

14. The lighting disinfection system according to claim 13, wherein the angle is adjustable by changing the orientation of the disinfection light source.

15. The lighting disinfection system according to claim 13, wherein the angle is adjustable by changing the orientation of the illumination source.

16. The lighting disinfection system according to claim 8, wherein the disinfection system comprises two laser emitters mounted at two edges of the cover for emitting laser beams to mark a disinfection range on an irradiate object.

17. The system according to claim 8, wherein the disinfection light source is a UV light.

18. The system according to claim 8, wherein the illumination source comprises an illumination source chip mounted within the light system housing, and the diffusion hood is mounted on an opening of the light system housing in front of the corresponding illumination source chip in the front part of the system housing.

* * * * *